(12) United States Patent
Inoue et al.

(10) Patent No.: US 10,572,995 B2
(45) Date of Patent: Feb. 25, 2020

(54) INSPECTION METHOD AND INSPECTION APPARATUS

(71) Applicant: NuFlare Technology, Inc., Yokohama-shi (JP)

(72) Inventors: Hiromu Inoue, Yokohama (JP); Nobutaka Kikuiri, Koganei (JP)

(73) Assignee: NuFlare Technology, Inc., Yokohama-shi (JP)

( * ) Notice: Subject to any disclaimer, the term of this patent is extended or adjusted under 35 U.S.C. 154(b) by 125 days.

(21) Appl. No.: 15/947,090

(22) Filed: Apr. 6, 2018

(65) Prior Publication Data
US 2018/0232873 A1 Aug. 16, 2018

Related U.S. Application Data

(63) Continuation of application No. PCT/JP2016/081707, filed on Oct. 26, 2016.

(30) Foreign Application Priority Data

Oct. 27, 2015 (JP) ................................ 2015-211244

(51) Int. Cl.
*G06T 7/00* (2017.01)
*G03F 1/84* (2012.01)
*G01N 21/956* (2006.01)

(52) U.S. Cl.
CPC .......... *G06T 7/001* (2013.01); *G01N 21/956* (2013.01); *G01N 21/95607* (2013.01); *G03F 1/84* (2013.01); *G01N 2021/95676* (2013.01); *G06T 2207/30148* (2013.01)

(58) Field of Classification Search
CPC .......... G06T 7/001; G06T 2207/30148; G01N 21/956; G01N 21/95607; G01N 2021/95676; G03F 1/84
See application file for complete search history.

(56) References Cited

U.S. PATENT DOCUMENTS

| 2011/0188734 A1* | 8/2011 | Tsuchiya | ............... G06T 7/0002 382/149 |
| 2012/0134542 A1* | 5/2012 | Pang | ...................... G06T 7/001 382/106 |

FOREIGN PATENT DOCUMENTS

| JP | 2001-235853 | 8/2001 |
| JP | 2001-516898 | 10/2001 |

(Continued)

OTHER PUBLICATIONS

International Search Report dated Jan. 24, 2017 in PCT/JP2016/081707, filed Oct. 26, 2016( with English Translation).

(Continued)

*Primary Examiner* — Menatoallah Youssef
(74) *Attorney, Agent, or Firm* — Oblon, McClelland, Maier & Neustadt, L.L.P.

(57) ABSTRACT

A high resolution optical image is acquired by irradiating a mask with light emitted by a light source via a high resolution optical system. A low resolution optical image is acquired by irradiating the same mask with the light via a low resolution optical system. The design data of the mask pattern is corrected in light of shapes and dimensions determined according to at least one of a manufacturing process of the mask and a manufacturing process of a semiconductor device to be manufactured by transferring the mask pattern to a semiconductor wafer. Reference image data are generated corresponding to the high resolution optical image and the low resolution optical image. Whether the defect detected in the high resolution optical image is true or false is determined according to information of the defect detected in the low resolution optical image.

6 Claims, 6 Drawing Sheets

(56) References Cited

FOREIGN PATENT DOCUMENTS

| | | |
|---|---|---|
| JP | 2005-148320 | 6/2005 |
| JP | 2006-46943 | 2/2006 |
| JP | 2006-200944 A | 8/2006 |
| JP | 2009-105430 | 5/2009 |
| JP | 2009-109382 | 5/2009 |
| JP | 2010-223838 | 10/2010 |
| JP | 2011-221499 | 11/2011 |
| JP | 2012-252055 | 12/2012 |
| JP | 2014-206466 | 10/2014 |
| KR | 10-2008-0052446 A | 6/2008 |

OTHER PUBLICATIONS

Written Opinion dated Jan. 24, 2017 in PCT/JP2016/081707, filed Oct. 26, 2016.

H. H. Hopkins, "On the diffraction theory of optical images", In Proc. Royal Soc. Series A., vol. 217, No. 1131, 1953, Pages 9.

N. B. Cobb, "Fast Optical and Process Proximity Correction Algorithms for Integrated Circuit Manufacturing" A dissertation submitted in partial satisfaction of the requirements for the degree of Doctor of Philosophy in Engineering: Electrical Engineering and Computer Science in the Graduate Division of the University of California at Berkeley, 1988, pp. 139.

Carl Hess et al., "A Novel Approach: High Resolution Inspection with Wafer Plane Defect Detection" Proc. of SPIE vol. 7028, 2008, pp. 11.

Karen D. Badger, et al., "From Nightmares to Sweet Dreams—Inspection of aggressive OPC on 14 nm reticles (and beyond) using a novel high-NA and low-NA dual method" Proc. SPIE vol. 9635, 963511-1, 2015, pp. 12.

Korean Office Action dated Jun. 17. 2019 in Korean Patent Application No. 10-2018-7011459 (with unedited computer generated English translation), 11 pages.

\* cited by examiner

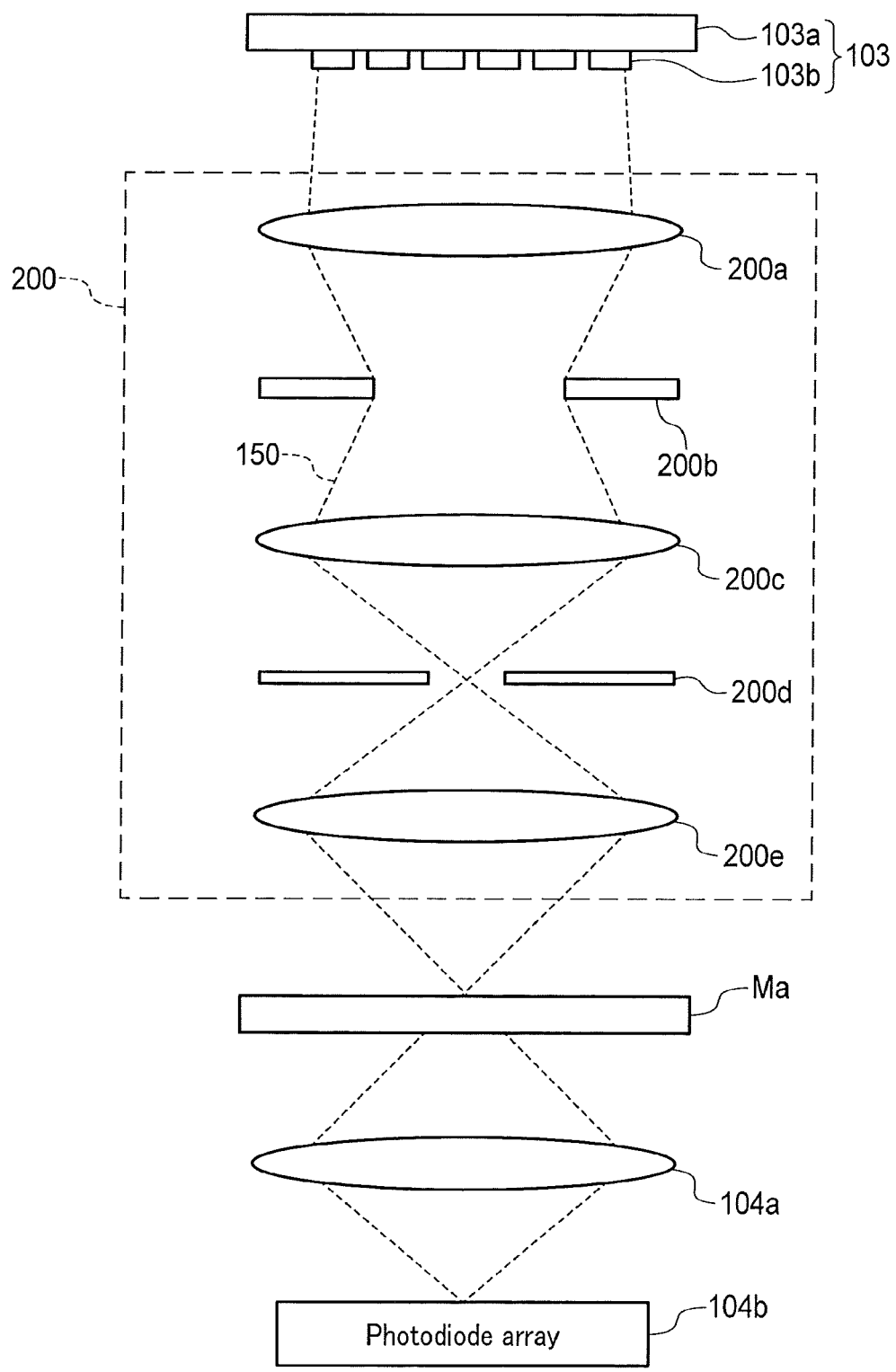
F I G. 2

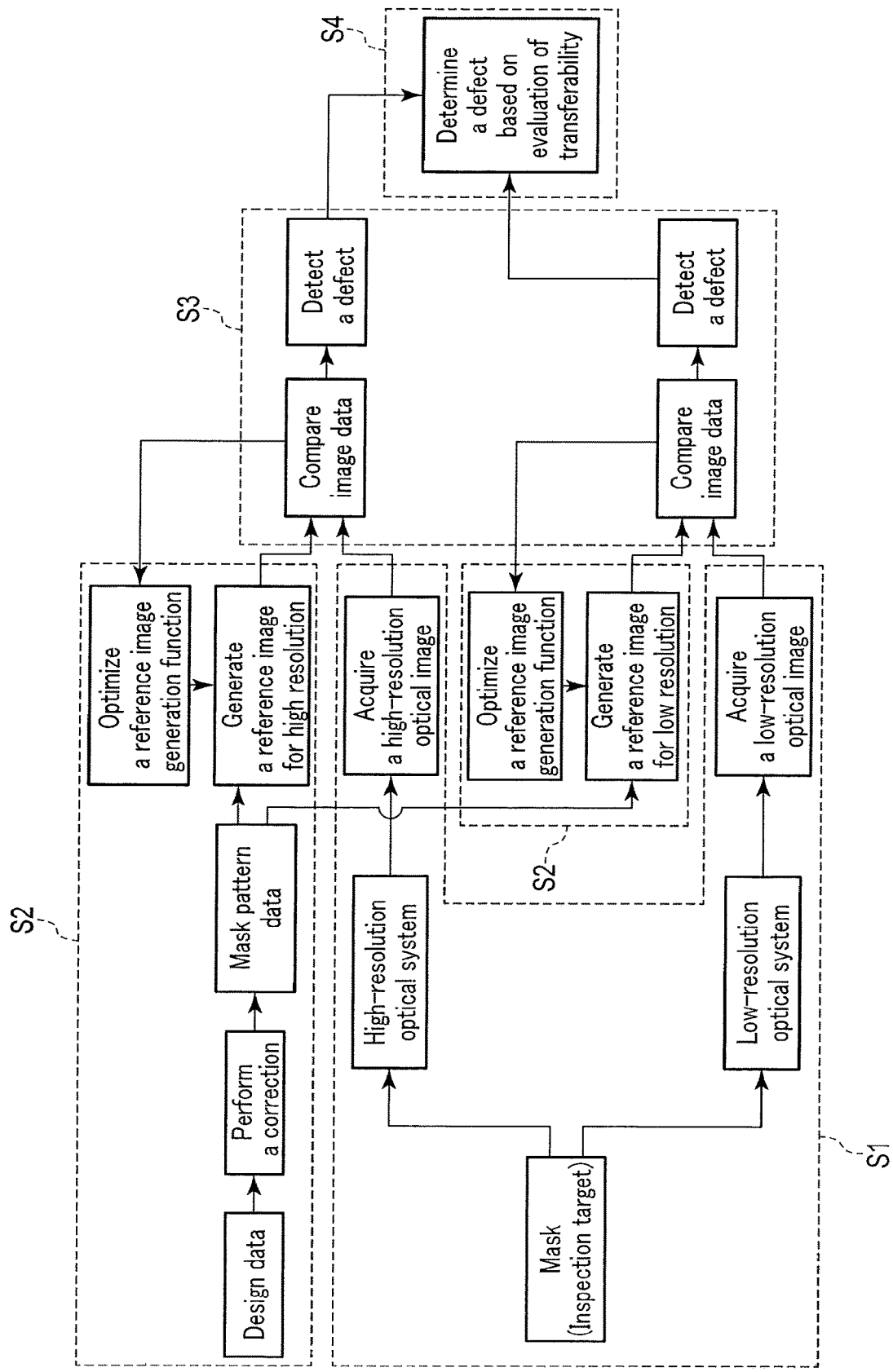
F I G. 4

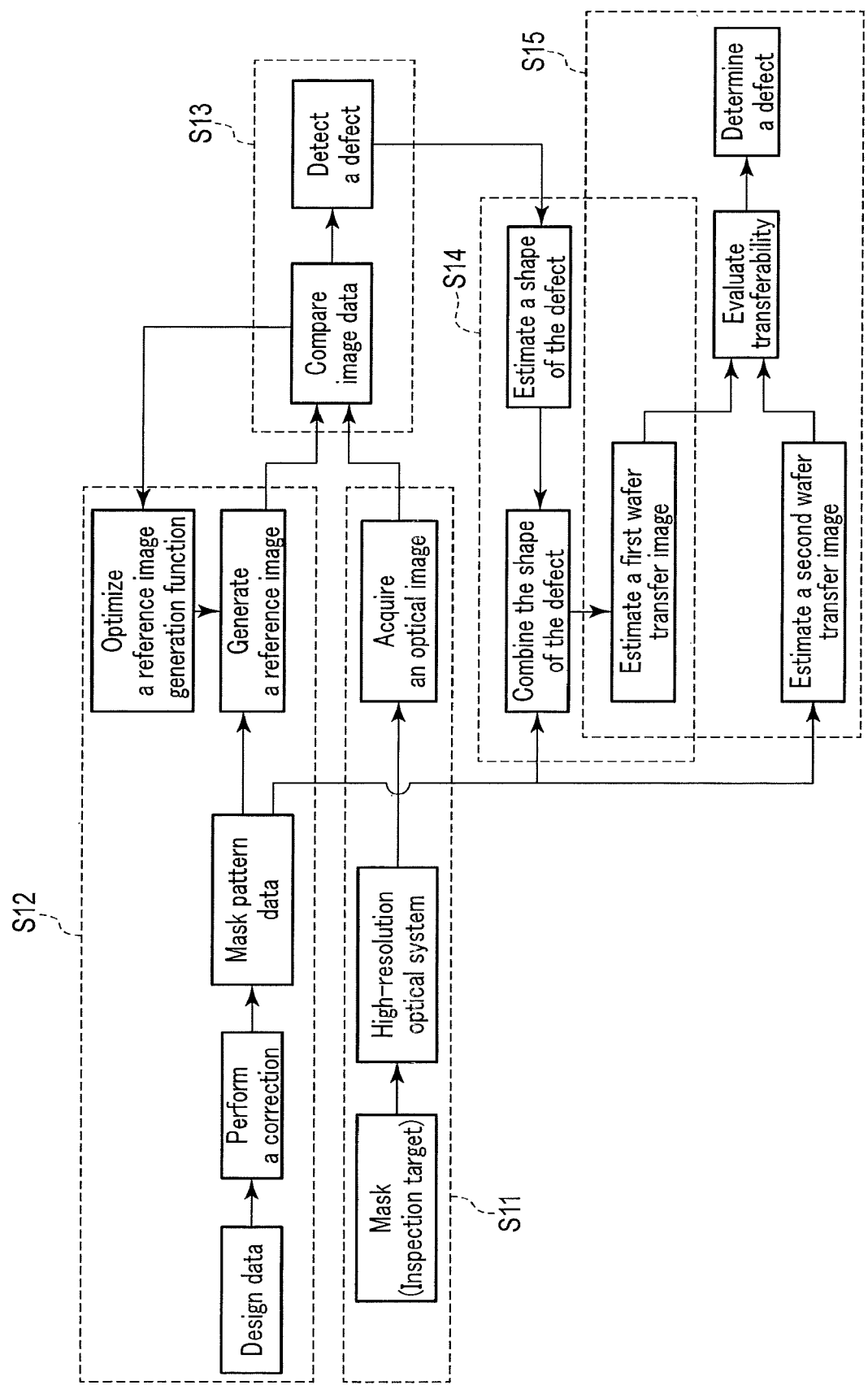
F I G. 6

INSPECTION METHOD AND INSPECTION APPARATUS

CROSS-REFERENCE TO RELATED APPLICATION

This application is based upon and claims the benefit of priority from Japanese Patent Application No. 2015-211244, filed Oct. 27, 2015, and PCT International Application No. PCT/JP2016/081707, filed Oct. 26, 2016, the entire contents of which are incorporated herein by reference.

FIELD

The present invention relates generally to an inspection method and an inspection apparatus, and specifically relates to an inspection method and an inspection apparatus to inspect a mask by the Die-to-Database comparison.

BACKGROUND

In a manufacturing process of a semiconductor device, a pattern formed on a mask is transferred to a wafer (semiconductor substrate) using a reduction projection exposure apparatus. Specifically, an exposure apparatus called a stepper or a scanner decreases a circuit pattern provided on the mask in size from about one-fourth to one-fifth and projects the pattern onto the wafer.

Recently, along with high accumulation and high capacity of Large-scale integrated circuits (LSI), the width of circuit lines required for semiconductor devices is ever narrowing. Along with this tendency, the width of the lines of a pattern formed on a mask is getting narrower. For example, in recent typical logic devices, it is required to form a pattern having a line width of several ten nanometers.

Manufacturing the LSIs incurs large costs. For this reason, it is important to increase a yield rate in a manufacturing process. Examples of major factors that decrease a fabrication yield of LSIs include a defect of a pattern formed on a mask, and a fluctuation of processing conditions in a manufacturing process of a semiconductor device. To eliminate the factors, the defect of the mask is detected through an inspection, or a margin is provided for the fluctuation of the processing conditions.

A method of ensuring the margin for the fluctuation of the processing conditions includes an improvement in dimensional accuracy of the pattern of the mask. As described above, miniaturization of the pattern of the mask is ongoing. For the reasons described above, in the inspection of the mask, it is required to detect a difference in shape and dimensions of a fine pattern as a defect. Specifically, it is required to detect a shape defect, such as a short-circuit defect in which lines are short-circuited and an open defect in which a line is disconnected, and a defect caused by an inappropriate gap between adjacent patterns due to linewidth abnormality of the pattern or a positional deviation of the pattern.

As one of methods of forming a fine circuit pattern, there is the Optional Proximity Correction (OPC) technique. The OPC technique is used to preliminarily correct a pattern to be formed on a mask so that a pattern to be formed on a wafer matches with the design pattern.

In the OPC technique, an assist pattern is arranged on the side of a main pattern. With this, light energy of light incident on an area of the main pattern is ensured, and the formability of the main pattern on the wafer is improved. The assist pattern is not transferred to the wafer, and thus even if a defect is detected in the assist pattern in the inspection of the mask, the defect does not result in a practical problem. Therefore, such a defect should be distinguished as a fault defect from a true defect.

However, in masks of recent times in which the miniaturization advances, it becomes difficult to distinguish between the true defect and the fault defect. That is, it is difficult to determine whether a detected defect is a defect that should be detected as a true defect simply by comparing reference image data generated based on the design data with optical image data of the pattern acquired by the inspection apparatus.

It is proposed to incorporate simulation into the method of determining a defect.

For example, Japanese Patent Application KOKAI Publication No. 2012-252055 describe an inspection method in which simulation of the optical system of the inspection apparatus is performed to obtain information on the shape of the pattern of the mask which is to be detected when the mask is inspected by the inspection apparatus. It is determined whether or not a result of the inspection is within an acceptable range, using the information.

Japanese Patent Application KOKAI Publication No. 2009-105430 discloses a method of simulating a lithographic design including a number of polygons arranged in a predetermined region. Specifically, in Japanese Patent Application KOKAI Publication No. 2009-105430, FIG. 4 illustrates that a spacial image is generated using a bit map image on a basis of polygon design data (Box 126), and resist-modeling or simulation is executed by using the spacial image (Box 128). Further, FIG. 7 of Japanese Patent Application KOKAI Publication No. 2009-105430 disclose a technique of estimating, by simulation, the spacial image of the wafer based on the optical image obtained by the mask inspection apparatus. These techniques may identify correctness and defectiveness in the spacial image of the wafer or in the feature of the wafer obtained as a result of the wafer generation process, such as a reaction of a photoresist by means of exposure light.

Japanese PCT National Publication No. 2001-516898 describes 1) in the mask inspection system, it is important to determine whether or not a defect under a specific condition in the lithographic process is transferred to a photoresist in the lower layer; 2) if the defect of the mask is not printed or does not influence the lithography process, acceptable lithography can be achieved even by use of the mask including the defect. Japanese PCT National Publication No. 2001-516898 further discloses the inspection apparatus that receives a defective area image including a part of the mask image to generate a simulated image. This simulated image includes a simulation of an image transferred to the wafer.

However, the simulation requires various parameters, and has difficulties in which setting of a threshold to distinguish between a true defect and a fault defect becomes ambiguous. Further, there is also a difficulty that a difference between the simulation result and the actual inspection result occurs depending on the type of a pattern to be formed on the mask or the quality of the mask.

SUMMARY

The present invention is provided in consideration of such circumstances. Namely, an object of the present invention is to provide an inspection method and an inspection apparatus that can perform an accurate inspection while reducing fault defects.

Other objects and advantages of the present invention will be clear from the following descriptions.

A first embodiment of the present invention relates to an inspection method which comprises:

acquiring first optical image data of a pattern arranged on a mask by irradiating the mask with light emitted by a light source via a first optical system and directing the light transmitted through or reflected by the mask to be incident on an imaging device;

acquiring second optical image data of the pattern by irradiating the mask with light emitted by the light source via a second optical system and directing the light transmitted through or reflected by the mask to be incident on the imaging device, wherein the second optical system has a resolution lower than the first optical system and simulates an optical system of an exposure apparatus to be used to transfer the pattern of the mask to a semiconductor wafer;

generating first reference image data corresponding to the first optical image data and second reference image data corresponding to the second optical image data based on corrected design data, wherein the corrected design data is created by correcting design data for the pattern of the mask in light of shapes and dimensions of the pattern of the mask determined according to at least one of a manufacturing process of the mask and a manufacturing process of a semiconductor device to be manufactured by transferring the pattern of the mask on the semiconductor wafer;

detecting a defect of the pattern in the first optical image data by comparing the first optical image data with the first reference image data;

detecting a defect of the pattern in the second optical image data by comparing the second optical image data with the second reference image data; and determining whether the detected defect in the first optical image data is a true defect or a false defect in reference to information of the detected defect in the second optical image data and evaluating transferability of the detected defect to the semiconductor wafer.

In the first embodiment of the present invention, it is preferred that the shapes and the dimension of the pattern determined according to the manufacturing process of the semiconductor device are estimated based on a difference between a measured value and a design value of dimensions of a certain portion of the pattern of the mask.

In the first embodiment of the present invention, it is preferred that:

generating the first reference image data and the second reference image data includes filtering an image data created based on the corrected design data, and the inspection method further comprising adjusting simulation of characteristics of the resolutions of the first optical system and the second optical system, and parameters of image generation of the imaging device so as to minimize each of a difference between the first optical image data and the first reference image data and a difference between the second optical image data the second reference image data.

A second embodiment of the present invention relates to an inspection method which comprises:

acquiring optical image data of a pattern arranged on a mask by irradiating the mask with light emitted by a light source via an optical system and directing the light transmitted through or reflected by the mask to be incident on an imaging device;

generating reference image data corresponding to the optical image data based on corrected design data, wherein the corrected design data is created by correcting design data for the pattern of the mask in light of shapes and dimensions of the pattern of the mask determined according to at least one of a manufacturing process of the mask and a manufacturing process of a semiconductor device to be manufactured by transferring the pattern of the mask to a semiconductor wafer;

detecting a defect of the pattern in the optical image data by comparing the optical image data with the reference image data;

estimating a shape of the defect to be transferred to the semiconductor wafer by use of an optical image data of the defect of the pattern detected in the optical image data, the reference data corresponding to the optical image data, and the corrected design data of the pattern, and estimating a first transfer image as transferred to the semiconductor wafer, based on data in which information on the estimated shape of the defect is added to the corrected design data, using a condition where the pattern arranged on the mask is transferred to the semiconductor wafer;

estimating a second transfer image of the pattern to be transferred on the semiconductor wafer, based on the corrected design data, by use of the condition where the pattern of the mask is transferred to the semiconductor wafer; and determining whether the detected defect is a true defect or a false defect by comparing the first transfer image and the second transfer image and evaluating transferability of the detected defect to the semiconductor wafer.

A third embodiment of the present invention relates to an inspection apparatus which comprises:

a light source;

a stage on which a mask is places;

an optical system having a variable numerical aperture and directing light emitted by the light source to irradiate the stage;

an imaging device that acquires optical image data of the mask placed on the stage by directing light emitted by the light source, through the optical system, and transmitted through or reflected by the mask to be incident on the imaging device;

a reference image generator that generates reference image data corresponding to the optical image data based on corrected design data, wherein the corrected design data is created by correcting design data for the pattern of the mask in light of shapes and dimensions of the pattern of the mask determined according to at least one of a manufacturing process of the mask and a manufacturing process of a semiconductor device to be manufactured by transferring the pattern of the mask to a semiconductor wafer;

a comparator that compares the optical image data with the reference image data to detect a defect of the pattern in the optical image data; and a defect analyzer that analyzes the defect detected in the comparator by comparing first optical image data acquired by the imaging device using the numerical aperture as a value that is required to detect a defect of the pattern with first reference image data generated by the reference image generator, based on information on a defect detected in the comparator by comparing a second optical image data acquired by the imaging device using the numerical aperture as a value that simulates an optical system of an exposure apparatus to be used to transfer the pattern to the semiconductor wafer with second reference image data generated by the reference image generator.

The first embodiment of the present invention provides an inspection method that can perform an accurate inspection while reducing fault defects.

The second embodiment of the present invention provides another inspection method that can perform an accurate inspection while reducing fault defects.

The third embodiment of the present invention provides an inspection apparatus that can perform an accurate inspection while reducing fault defects.

BRIEF DESCRIPTION OF THE DRAWINGS

FIG. 2 is a diagram showing one example of the configuration of an illumination optical system according to the first embodiment.

FIG. 4 is a flowchart of an inspection method according to the first embodiment.

FIG. 6 is a flowchart of an inspection method according to the second embodiment.

DETAILED DESCRIPTION

First Embodiment

Figure 1:
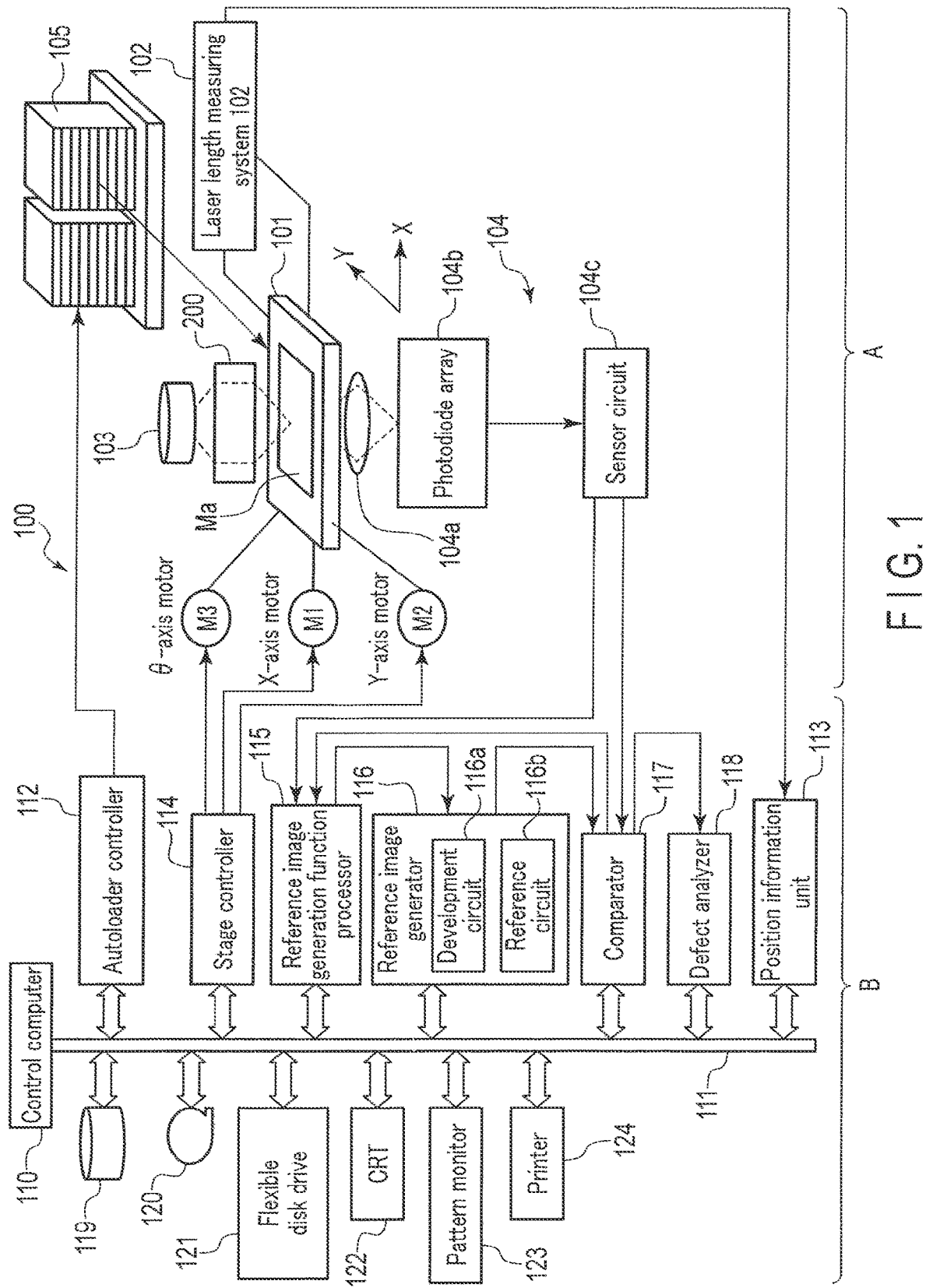
FIG. 1 is a schematic diagram of a configuration of an inspection apparatus according to a first embodiment.

FIG. 1 is a schematic diagram of a configuration of an inspection apparatus according to the present embodiment. As illustrated in FIG. 1, an inspection apparatus 100 comprises a configuration part A that acquires optical image data of an inspection target, and a configuration part B that performs processing necessary for the inspection using the optical image data acquired by the configuration part A. The configuration part A acquires an optical image of the inspection target to output optical image data corresponding to the optical image.

Examples of the inspection target include a mask used in photolithography. The mask has a configuration where a predetermined pattern is arranged on a main surface of a base material such as a transparent glass substrate. The configuration part A outputs optical image data corresponding to the pattern. In this specification, optical image data of a pattern of a mask may be simply referred to as optical image data of the mask. On the other hand, the configuration part B compares reference image data generated using a predetermined reference image generation function based on design data of the pattern of the mask with the optical image data output by the configuration part A to detect a defect of the pattern of the mask. In this specification, the pattern of the mask may be referred to as an inspection target pattern.

The configuration A comprises a stage 101 that can be driven in a horizontal direction (X-axis direction and Y-axis direction) and a rotational direction (θ-axis direction); a laser length measuring system 102 that measures a position of the stage 101; a light source 103 that emits light having a predetermined wavelength, an illumination optical system 200 that irradiates light from the light source 103 on a mask Ma; an imaging device 104 that generates optical image data of the mask Ma; and an autoloader 105 that places the mask Ma on the stage 101.

The stage 101 is driven by an X-axis motor M1, a Y-axis motor M2, and a θ-axis motor M3. These motors (M1, M2, and M3) are controlled by a stage controller 114. As a driving mechanism of motors, for example, air sliders and linear motors or stepping motors may be used in combination.

Although a detailed illustration is omitted, the laser length measurement system 102 includes a laser interferometer such as a Heterodyne interferometer. The laser interferometer measures positional coordinates of the stage 101 by applying and receiving laser light between respective mirrors for X-axis and for Y-axis provided at the stage 101. Measured data obtained by the laser length measurement system 102 is sent to a position information unit 113. The method of measuring the positional coordinates of the stage 101 is not limited to the method using the laser interferometer, and a method using a magnetic or optical linear encoder may be employed.

As for the light source 103, to allow an inspection of a defect of a mask for a device with a half pitch of 20 nm or less, a light source having a wavelength close to a wavelength of 193 nm used in photolithography is suitable. For example, a pulse laser that emits ultraviolet rays having a wavelength of 199 nm may be used.

FIG. 2 is a diagram showing an example of the configuration of the illumination optical system 200.

In FIG. 2, the light source 103 comprises a substrate 103a and a plurality of surface emitting laser elements 103b formed on the substrate 103a. For the substrate 103a, a silicon wafer is used, for example. The surface emitting laser elements 103b are elements that are formed on a silicon wafer in a manner similar to a manufacturing process of a semiconductor device and emit a fundamental wave of an ultraviolet ray.

The illumination optical system 200 comprises a light collecting lens 200a, an illumination diaphragm 200b, a focusing lens 200c, an aperture diaphragm 200d, and a condenser lens 200e. These components are arranged in a sequential order from the side of the light source 103 toward the mask Ma along an optical axis of light emitted from the light source 103. The order in which the components are arranged is not limited to the above-described order; for example, they may be arranged such that the illumination diaphragm 200b is located on the downstream side of the aperture diaphragm 200d. The illumination optical system 200 may comprise elements other than the components shown in FIG. 2. For example, the illumination optical system 200 may include a means that splits the light emitted from the light source 103 into an optical path that illuminates the mask Ma for transmission and an optical path that illuminates the mask Ma for reflection, a means that changes the light to circularly polarized light, linearly polarized light, etc., and a means that changes the shape of the light source to a point, an annular shape, etc.

Light emitted from the light source 103 is collected by the light collecting lens 200a and is then transmitted through the illumination diaphragm 200b. Thereafter, this light is brought into focus to the aperture diaphragm 200d by the focusing lens 200c. Light transmitted through the aperture diaphragm 200d is transmitted through the condenser lens 200e and then illuminates the mask Ma.

The distance between the condenser lens 200e and the mask Ma is adjusted to a distance in which an image of the illumination diaphragm 200b is formed on the surface of the mask Ma. The illuminated area on the surface of the mask Ma is changed by changing the size of the illumination diaphragm 200b. On the other hand, the aperture diaphragm 200d is located at a focal position of the condenser lens 200e. The light that forms an image at the aperture diaphragm 200d is transmitted through the condenser lens 200e, resulting in parallel light, and thus the light does not form an image on the surface of the mask Ma.

A numerical aperture NA of the illumination optical system 200 can be changed successively by changing the size of the aperture diaphragm 200*d*. The greater the numerical aperture NA, the higher the resolution, and the smaller the numerical aperture NA, the lower the resolution. In an inspection apparatus which requires high resolution, the numerical aperture NA of its optical system may be, for example, 0.75 to 0.85. In contrast, since the resolution of an exposure apparatus used for transferring a pattern provided on a mask Ma to a wafer (a semiconductor substrate) in a manufacturing process of a semiconductor device is lower than that of the inspection apparatus, the numerical aperture of its optical system may be, for example, 0.3 to 0.35.

In the present embodiment, the numerical aperture NA of the illumination optical system 200 is changed by changing the size of the aperture diaphragm 200*d*. A high resolution optical system (a first optical system) for the optical system of the inspection apparatus and a low resolution optical system (a second optical system) that simulates the optical system of the exposure apparatus are selected, and then an optical image of a pattern of the mask Ma is acquired. Thus, an optical image captured by the high resolution optical system (which may be referred to as a high resolution optical image, hereinafter) and an optical image captured by the low resolution optical system (which may be referred to as a low resolution optical image, hereinafter) are obtained. The configuration of the inspection apparatus 100 is not limited to the configuration that realizes a high resolution optical system and a low resolution optical system in one optical system as described above, and the inspection apparatus 100 may be configured to include two optical systems, i.e., a high resolution optical system and a low resolution optical system.

The imaging device 104 comprises a light convergent lens 104*a* that converges light transmitted through the mask Ma to form an optical image of the pattern of the mask Ma; a photodiode array 104*b* that photo-electrically converts the optical image; and a sensor circuit 104*c* that converts analog signals output from the photodiode array 104*b* into digital signals for the optical image data and outputs them. For the photodiode array 104*b*, for example, Time Delay Integration (TDI) sensors are provided. The imaging device 104 may be configured such that the focal point is automatically adjusted by an autofocus mechanism (not illustrated).

Returning to FIG. 1, the configuration part B comprises a control computer 110 that controls the entirety of the inspection apparatus 100; a bus 111 that serves as a data transmission path; an autoloader controller 112 connected to the control computer 110 via the bus 111; a position information unit 113; a stage controller 114, a reference image generation function processor 115, a reference image generator 116, a comparator 117, a defect analyzer 118, a magnetic disk drive 119 which is one example of a main storage unit; a magnetic tape device 120 which is one example of an auxiliary storage unit; a flexible disk drive 121 which is another example of an auxiliary storage device; a CRT 122 which is one example of a display, a microscope pattern monitor 123 using an ITV camera that is another example of a display, and a printer 124.

FIG. 1 illustrates components required by the present embodiment; however, other known components necessary for an inspection may be included. Those described as " . . . unit", " . . . er" or " . . . or" in the specification of the present application can be configured by one or more programs operable in a computer; however, they may be implemented not only in a software program or software programs but also in a combination of software with hardware or with firmware. If those components are implemented in programs, the programs are stored in a storage device or devices such as a magnetic disk drive. For example, the autoloader controller 112 may be implemented in an electric circuit or may be implemented in software executable by the control computer 110. It may also be realized by a combination of an electric circuit and software.

Next, one example of a method of inspecting a mask Ma using the inspection apparatus 100 shown in FIG. 1 will be explained.

The inspection method according to the present embodiment comprises acquiring optical image data (S1); generating reference image data (S2); detecting a defect (S3), and analyzing the defect (S4). Hereinafter, each of the steps described above will be explained in reference to the drawings.

(1) Acquiring Optical Image Data (S1)

In the present embodiment, an optical image captured by a high resolution optical system (a first optical system) and an optical image captured by a low resolution optical system (a second optical system) for the same pattern of the mask Ma are acquired by changing the numerical aperture NA of the illumination optical system 200 in the inspection apparatus 100.

In FIG. 1, first, a mask Ma is placed on the stage 101 by the autoloader 105. The autoloader 105 is driven by the autoloader controller 112. The operation of the autoloader controller 112 is controlled by the control computer 110. The mask Ma is fixed on the stage 101 by means of a vacuum chuck, etc.

When the mask Ma is placed on the stage 101, the mask Ma is irradiated with light. Specifically, the light emitted from the light source 103 is applied to the mask Ma via the illumination optical system 200. If the size of the aperture diaphragm 200*d* shown in FIG. 2 is for the high resolution optical system, a high resolution optical image is captured. On the other hand, if the size of the aperture diaphragm 200*d* is for the low resolution optical system, a low resolution optical image is captured.

As explained above, the size of the aperture diaphragm 200*d* and the numerical aperture NA of the illumination optical system 200 have correlation with each other. Specifically, if the aperture of the aperture diaphragm 200*d* is decreased, the condition for an incident angle is more narrowly restricted, and the numerical aperture NA is increased. Thus, the sensitivity of detecting a defect is improved. On the other hand, if the aperture of the aperture diaphragm 200*d* is increased, an image is captured in conditions of a wider incident angle, and the numerical aperture decreases. Thus, the sensitivity of detecting a defect degrades.

In the present embodiment, the numerical aperture NA of the high resolution optical system, i.e. the size of the aperture diaphragm 200*d* corresponding to the numerical aperture NA (e.g., 0.75 to 0.85) of the optical system of the inspection apparatus, is pre-determined. The numerical aperture NA of the low resolution optical system, i.e. the size of the aperture-stop 200*d* corresponding to the numerical aperture NA (e.g., 0.3 to 0.35) of the optical system of the exposure apparatus used for transferring a pattern provided on the mask Ma to the wafer is also pre-determined. When an optical image is captured, the size of the aperture diaphragm 200*d* is selected to capture the high resolution optical image or the low resolution optical image.

To obtain an accurate inspection result, the pattern of the mask Ma needs to be aligned at a predetermined position on the stage 101. For example, an alignment mark for positional alignment is provided on the mask Ma, and an image of the alignment mark is actually captured by the imaging device 104 to align a position of an inspection target pattern of the mask Ma on the stage 101. In the present embodiment, the alignment of the inspection target pattern of the mask Ma relative to the stage 101 is referred to as plate alignment.

For example, assume that cross-shaped mask alignment marks MA are provided at positions corresponding to each vertex of a rectangle and near four corners of the inspection target pattern of the mask Ma. Additionally, assume that a plurality of chip patterns are formed on the mask Ma, and a chip alignment mark CA is also provided for each chip. Further, assume that the stage 101 is configured by an X-Y stage that moves in a horizontal direction and a θ stage that is disposed on the X-Y stage and moves in a rotational direction. Specifically in this case, the positional alignment includes aligning the X-axis and a Y-axis of the inspection target pattern with the traveling axis of the X-Y stage while the mask Ma is placed on the stage 101.

First, of the mask alignment marks Ma provided at the four places, images of two mask alignment marks Ma having smaller values of Y-coordinate are captured, and fine adjustment is performed in the rotational direction of the masks Ma by rotating the θ stage so that both of the two marks take the same Y coordinate accurately. In this process, the distance between the two mask alignment marks MA are also measured accurately. Next, images of two mask alignment marks MA having larger values of Y coordinate are captured. As such, coordinates of all of the four mask alignment marks Ma are measured accurately.

From the measurements described above, at vertices of a rectangle that has the two mask alignment marks MA having smaller values of Y coordinate at both ends of the base of the rectangle, the other two mask alignment marks Ma having larger values of Y coordinate are positioned. There may be a case where the mask alignment marks Ma create a deformed rectangular shape due to deviation of the measured coordinates of the two mask alignment marks Ma that should be positioned at each vertex coordinate of the rectangle, and the distance between the measured alignment marks is expanded or contracted relative to the designed distance between the coordinates. Then, it is presumed that an area of a pattern to be inspected is also deformed and extended or contracted similarly to that rectangle. Thus, a correction reflecting the deviation is performed when reference image data is generated at the reference image generator 116.

The mask Ma may not necessarily include the mask alignment marks MA. In this case, alignment may be performed using vertices of corners or sides of edge patterns in the pattern of the mask MA, which are present as near the circumference of the mask Ma as possible and have the same X-Y coordinates.

The inspection target area (the area in which the inspection target pattern is provided) of the mask Ma is virtually divided into a plurality of strip-shaped regions. The strip-shaped regions are referred to as stripes. Each of the stripes may have an area of several hundred micrometers in width, and of about 100 mm in length corresponding to the total length of the inspection target area of the mask Ma in the X-direction.

Furthermore, a plurality of sections for imaging targets that are divisions into grids (hereinafter, each imaging target section is represented as "frame") are virtually set in each stripe. It is appropriate that each frame has a size of a square having a width of the stripe or a quarter of the width of the stripe.

Figure 3:
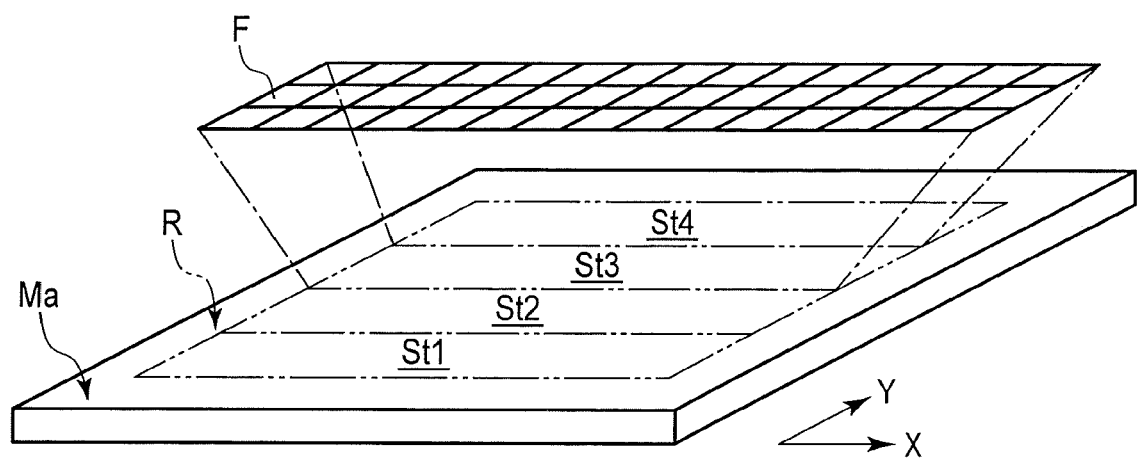
FIG. 3 is a schematic diagram showing the relationship of an inspected area of a mask with stripes and frames.

FIG. 3 is a schematic diagram showing the inspection target area R in the mask Ma, and the relationship between the stripes (St1 to St4) and the frames F. In this example, the inspection target area R in the mask Ma is virtually divided into four stripes St1 to St4, and furthermore, 45 frames F are virtually set for each of the stripes St1 to St4.

The stripes St1 to St4 form a line in the Y-axis direction. On the other hand, each frame has a rectangular shape, for example, of about more than ten square micrometers. To avoid failure in capturing images, two adjacent frames are set so that an edge of one frame overlaps an edge of the other frame with a predetermined width. The predetermined width may be set to be a width of about 20 pixels in reference to, for example, the pixel size of the photodiode array 104b. The stripes are set similarly so that edges of adjacent stripes overlap each other.

An optical image of the mask Ma is captured for each stripe. That is, the operation of the stage 101 is controlled so that each of the stripes St1, St2, St3, and St4 are sequentially scanned when an optical image is captured in the example shown in FIG. 3. Specifically, first, optical images in stripe St1 are captured sequentially in the X-direction, while the stage 101 moves in the −X-direction in FIG. 3. The optical images are sequentially applied to the photodiode array 104b in FIG. 1. Upon completion of the image-capturing of the optical images of stripe St1, optical images of stripe St2 are then captured. At this time, after the stage 101 moves stepwise in the −Y-direction, the stage 101 moves in a direction (X-direction) opposite to the direction of the image capturing of stripe St1 (−X-direction). The captured optical images of stripe St2 are also sequentially applied to the photodiode array 104b. In a case where optical images of stripe St3 are captured, the stage 101 moves stepwise in the −Y-direction, and then the stage 101 moves in a direction opposite to the direction of capturing the optical images of stripe St2 (X-direction), i.e., in the direction (−X direction) along which the optical images of stripe St1 are captured. Optical images of stripe St4 are also captured in the same manner.

After light transmitted through the mask Ma forms an image as the optical image of the pattern of the mask Ma by the imaging device 104, it is subjected to A/D (analog/digital) conversion, and then is output as the optical image data. Specifically, the photodiode array 104b captures the optical images of the mask Ma and sequentially outputs analog signals corresponding to the optical images in a sensor circuit 104c. The sensor circuit 104c converts the analog signals output by the photodiode array 104b respectively to digital signals as optical image data and outputs them.

It should be noted that the optical image data is input to a digital amplifier (not illustrated) which is provided in the sensor circuit 104c and is offset/gain-adjustable on a pixel to pixel basis. A gain for each pixel of the digital amplifier is determined by calibration. For example, in calibration for transmitted light, a black level is determined during capturing images of a light-shade area of the mask Ma which is sufficiently wide relative to an area for which an image is captured by the imaging device 104. Next, a white level is determined during capturing images of a light transmissible area of the mask Ma which is sufficiently wide relative to the area for which an image is captured by the imaging device 104. At this time, taking deviation in optical intensity during the inspection into consideration, an offset and a gain are adjusted on a pixel to pixel basis so that the amplitude of the white level and the black level ranges from 10 to 240 of 8-bit gray-scale data which corresponds to about 4% to about 940 of the gray-scale data.

FIG. 4 is a flowchart of the inspection method according to the present embodiment. The portions each corresponding to each of the steps of acquiring optical image data (S1), generating reference image data (S2), detecting a defect (S3), and analyzing the defect (S4) are enclosed by dotted lines in the figure to be identified.

As shown in FIG. 4, in acquiring optical image data (S1), when the high resolution optical system is used for the illumination optical system 200, high resolution optical images are captured, and high resolution optical image data (first optical image data) is acquired. On the other hand, a low resolution optical system is used for the illumination optical system 200, low resolution optical images are captured, and low resolution optical image data (second optical image data) is acquired.

(2) Generating Reference Image Data (S2)

Reference image data is generated based on the design data (designed pattern data) of the pattern of the mask Ma. The reference image data is data to be compared with the optical image data and used as a reference for determining presence or absence of a defect in the optical image data, in the inspection based on the Die to Database comparison. In the present embodiment, the reference image data (first reference image data) corresponding to the optical image data (first optical image data) obtained by the high resolution optical system, and the reference image data (second reference image data) corresponding to the optical image data (second optical image data) obtained by the low resolution optical system are generated.

In a manufacturing process of the mask and a manufacturing process of the semiconductor device, the shapes and dimensions of the pattern of the mask are determined depending on a manufacturing recipe and process conditions so that deviation in shapes and dimensions of the pattern are reduced when the pattern is transferred to a wafer. Namely, the degree of roundness of corners and the width of the finished lines of the pattern of the mask are accommodated. In the present embodiment, corrections are made on the design pattern data to reflect the accommodations of the shapes and the dimensions determined depending on the manufacturing recipe and the process conditions. The reference image data is generated using the corrected design pattern data. The following are specific examples of the corrections in the design pattern data.

<Change in Manufacturing Process of Mask>

In forming the pattern on the mask, an electron beam lithographic technique is used. According to an electron beam lithographic apparatus used in the technique, data of a circuit pattern which is complicated and discretionally designed is processed, and the circuit pattern is drawn on a resist film. There is a case where the shapes of the drawn pattern have a special tendency in characteristics depending on the electric beam lithographic apparatus. For example, the degree of roundness of corner portions of the pattern, and the tendency of thickening and thinning of the width of the pattern lines on the mask surface vary depending on types or individual differences of electronic beam lithographic apparatuses used. Therefore, in the manufacturing process of the mask, the shapes and dimensions of the mask pattern are adjusted so as to reduce the roundness and the line width error. In the present embodiment, corrections in which such adjustments are reflected are made in the design pattern data.

Figures drawn on the mask by the electronic beam lithographic apparatus corresponds to an energy accumulated distribution image of an electronic beam. In the manufacturing process of the mask, proximity corrections are made on the drawn pattern using the energy accumulated distribution image to compensate deviations in the position and the dimensions of the pattern to be drawn. In the present embodiment, corrections in which such compensations are reflected are performed in the design pattern data.

<Change in Manufacturing Process of Semiconductor Device>

In the manufacturing process of the semiconductor device, a resist film is provided on the main surface of the wafer. The pattern of the mask is transferred to the resist film by the exposure apparatus. Thereafter, a resist pattern is formed by developing the resist film. Next, the main surface of the wafer is selectively etched using the resist pattern as shields. In this process, in the pattern created by etching, for example, a distortion from the transferred image on the wafer is produced. Therefore, in the manufacturing process of the semiconductor device, the proximity corrections using a micro-loading effect image by etching are performed to compensate the shapes and the dimensions of the pattern to be created by etching. In the present embodiment, corrections in which such compensations are reflected are performed in the design pattern data.

If the process conditions in the manufacturing process of the semiconductor device are not known, the process conditions for a predetermined pattern (e.g., a typical pattern) of the mask can be estimated by measuring dimensions of the pattern using, for example, a Scanning Electron Microscope (SEM). In other words, since the shapes and the dimensions of the pattern of the mask determined in the manufacturing process of the semiconductor device can be known from a result of the measurements of dimensions, the design pattern data is corrected using differences between the measured values and the design values of the dimensions of the certain pattern.

The correction process for the design pattern data may be performed inside or outside the inspection apparatus 100. The corrected design pattern data is stored, for example, in the magnetic disk drive 119 in the inspection apparatus 100 shown in FIG. 1. The control computer 110 reads the corrected design pattern data out and sends it to the reference image generator 116.

The reference image generator 116 comprises a development circuit 116a and a reference circuit 116b. The corrected design pattern data is converted into binary or multiple level image data in the development circuit 116a.

The image data is sent from the development circuit 116a to the reference circuit 116b. The reference circuit 116b performs a filter processing on the image data. For example, the optical image data obtained by the imaging device 104 in FIG. 1 is in a blur state due to resolution characteristics of the illumination optical system 200 or an aperture effect of the photodiode array 104b, in other words, in a state where a spacial low-pass filtering is applied to the data. Therefore, processing for making the reference image data resemble the optical image data is performed by filter processing, for example, by performing simulations of the illumination optical systems 200 of high resolution and of low resolution or by adjusting image-forming parameters at the photodiode array 104b. In this process, it is preferred to adjust the simulations and the image-forming parameters to minimize a difference between the high resolution optical image data and the reference image data corresponding to the high resolution optical image data. Similarly, it is preferred to adjust the simulations and the image-forming parameters to minimize a difference between the low resolution optical image data and the reference image data corresponding to the low resolution optical image data.

When the simulation and image-forming parameters are adjusted to minimize a difference between the high resolution optical image data and the reference image data corresponding to the high resolution optical image data and a difference between the low resolution optical image data and the reference image data corresponding to the low resolution optical image data, it is preferred to also adjust the position of a light-receiving surface of the photodiode array 104b. On this occasion, it is more preferred to take a focus-offset amount into account.

The focus offset amount means the amount of deviation from a focal point. It is known that in the defect inspection, there may be a case where the signal-to-noise (S/N) ratio in the defect inspection is more improved by inspection with a certain distance (focus offset) intentionally provided from the focal point. Therefore, a focal point of the best contrast of the optical image is obtained. Next, an inspection is performed by setting a position, as an optimum focal position, at which the focus offset is applied to the focal point for correction. Specifically, the position of the light-receiving surface of the photodiode array 104b is adjusted to be the position where the focus offset is applied to the focal point for correction.

In the filtering process, a reference image generation function that simulates the resolution characteristics of the illumination optical system 200 and the aperture effect of the photodiode array 104b is determined. In the present embodiment, the reference image generation function is determined by the reference image generation function processor 115. Specifically, the corrected design pattern data is read out from the magnetic disk drive 119 by the control computer 110 and is sent to the reference image generation function processor 115. The optical image data output from the imaging device 104 is also sent to the reference image generation function processor 115. In the reference image generating function processor 115, a reference image generation function suitable for the reference image data corresponding to the high resolution optical image data and a reference image generation function suitable for the reference image data corresponding to the low resolution optical image data are determined based on the corrected design pattern data and the optical image data.

Next, each of the reference image generation functions is sent from the reference image generation function processor 115 to the reference image generator 116. Then, in the reference circuit 116b in the reference image generator 116, the image data output from the development circuit 116a is filtered using the reference image generation functions. With this configuration, the reference image data corresponding to the high resolution optical image data and the reference image data corresponding to the low resolution optical image data are generated.

(3) Detecting a Defect (S3)

In this step, first, in the comparator 117 shown in FIG. 1, the optical image data obtained in the acquisition process (S1) is compared with the reference image data obtained in the generation process (S2) to detect a defect. Specifically, this step is performed as follows.

First, the optical image data from the imaging device 104 and the reference image data from the reference image generator 116 are sent to the comparator 117, respectively. The position data obtained by measuring coordinates of the position of the stage 101 is sent from the position information unit 113 to the comparator 117.

According to the inspection apparatus 100 in FIG. 1, the imaging device 104 obtains an optical image of the mask Ma by convergence of the illumination light passed through the mask Ma, and thus the transmitted optical image data and the reference image data are compared in the comparator 117. If the inspection apparatus is configured to converge the illumination light reflected by the mask Ma to acquire the optical image of the mask Ma, the reflected optical image data and the reference image data are compared.

In the comparator 117, the optical image data is divided into segments of a predetermined size, and the reference image data is also divided like the optical image data. In the present embodiment, the optical image data is divided into data for respective frames. The reference image data is also divided into data for respective frames. In the following, each of optical image data divided for the frames is referred to as "optical frame data", and each of reference image data divided for the frames is referred to as "reference frame data".

In the comparator 117, the optical frame data and the reference frame data are compared with each other, and thereby a defect of the optical frame data is detected. Coordinate data of a position of the detected defect is created using the measured data sent from the position information unit 113.

In the comparator 117, several tens of comparators (not illustrated) are arranged. With this configuration, a plurality of optical frame data are simultaneously processed in parallel using respective corresponding reference frame data. Each of the comparators includes a frame alignment unit, an algorithm comparison processor, and a defect registration unit. When each comparator finishes processing of data of one optical frame, it fetches in unprocessed data of another optical frame and reference frame data corresponding to the data of another optical frame. In this way, a number of optical frame data are processed in a sequential order, and a defect is or defects are detected.

Specifically, first, the optical frame data and the reference frame data corresponding to the optical frame data are output in a set to each of the comparators. Then, the optical frame data and the reference frame data are aligned (frame alignment). In this process, the alignment is performed by shifting the optical or reference frame data parallelly on a pixel-to-pixel basis (a pixel of the photodiode array 104b) so that the positions of the edges of the pattern or the positions of peaks of brightness of the pattern are aligned. The alignment may also be performed on a sub-pixel basis by proportionally allocating brightness values of adjacent pixels to one or more sub-pixels.

After completion of the alignment between the optical frame data and the reference frame data, defect detection is performed in accordance with an appropriate comparison algorithm. For example, an analysis of a difference in level on a pixel-to-pixel basis between the optical frame data and the reference frame data, a comparison of differentiation values of pixels at the pattern edges of the optical frame data and of the reference frame data, etc. are performed. If a difference between the optical image data and the reference image data exceeds a predetermined threshold, the relevant portion is determined to be a defect.

For example, thresholds used for a line width defect to be registered are provided for each of a dimensional difference (nm) and a dimensional rate (%), between the line widths (Critical Dimension: CD) of the optical image data and of the reference image data. For example, two thresholds are provided, for example, such that a threshold for the dimensional difference of the line widths is 16 nm, and a threshold for the dimensional rate is 8%. If the pattern of the optical image data has a line width of 200 nm and a dimensional difference of 20 nm from the reference image data, the dimensional difference and the dimensional rate are both greater than the respective thresholds, and thus it is determined that this pattern includes a defect.

Thresholds used in the determination of a defect may also be provided individually for a case where the line width of the optical image data is thicker than that of the reference image data and a case where the line width of the optical image data is thinner than that of the reference image data. Rather than for the line widths, thresholds are provided individually for a case where a width of a space (a distance between patterns) between lines is thicker than that of the reference image data and a case where the space width is thinner than that of the reference image data. Furthermore, with respect to a pattern of a hole shape, thresholds may be for a diametrical size of the hole and a dimensional rate of the diameter. In this case, thresholds may be provided for a cross-section in an X-direction and for a cross-section in a Y-direction of the hole.

Algorithms used in the defect detection may include, for example, a level comparison method and a differential comparison method, in addition to the above-mentioned method. In the level comparison method, brightness values of pixels in the optical frame data, i.e., brightness values in a region corresponding to the pixels of the photodiode array 104b are calculated. By comparing the calculated brightness values with the brightness values of the reference frame data, a defect is detected. In the differential comparison method, a difference (a change of values) of the brightness values of pixels at an edge of a fine pattern on optical frame data, for example, at an edge of a line pattern, is determined by differentiation. This difference (a change of values) is compared with a difference (a change of values) of the corresponding brightness values of the reference frame data, and thereby a defect is detected.

If it is determined that there is a defect in the optical frame data by the defect detection process in accordance with a comparison algorithm, information on the detect, such as the optical frame data having the defect, coordinate data of the position of the defect, the reference frame data compared with the optical frame data, etc. are registered. This registration can be performed, for example, by a detection registration unit (not illustrated) provided in the comparator 117.

The comparator 117 can repeat, multiple times, a series of comparing and determining operations including alignment of the positions of the frame data, detection of the defects, and counting the number of the detected defects, for each set of the optical frame data and the reference frame data corresponding to the optical frame data and for each comparison algorithm, while changing conditions for the alignment of the positions of the frame data, and register results of the defect detection in the comparing and determining operation in which the least number of defects are detected.

According to the above, the optical image data and the reference image data are sequentially fetched in the comparator 117, and compared with each other to perform the detection of a defect in the optical image data. In the present embodiment, the optical image data obtained by using the illumination optical system 200 as a high resolution optical system, and the optical image data obtained by using the illumination optical system 200 as a low resolution optical system are provided. A comparison using these optical image data is performed according to the flow chart shown in FIG. 4.

As shown in FIG. 4, the high resolution optical image data is compared with the high resolution reference image data corresponding to the high resolution optical image data. The low resolution optical image data is compared with the low resolution reference image data corresponding to the low resolution optical image data.

For example, if a number of fault defects are detected by the comparison, an instruction for re-determining a function is output from the comparator 117 to the reference image generation function processor 115. Then, the process returns to generation of the reference image data (S2), and the reference image generating function is re-determined in the reference image generation function processor 115. In this case, for example, the reference image generation function can be determined in such a manner that among points for learning in the inspection apparatus 100 by machine learning, learning points in a region where a number of fault defects are detected are treated as non-defective points. Thereafter, the re-determined reference image generation function is sent to the reference image generator 116, and the reference image data is generated again in the reference image generator 116. Then, the process proceeds again to the detecting a defect (S3), and in the comparator 117, the high resolution optical image data and the re-generated high resolution reference image data are compared with one another to detect a defect, or the low resolution optical image data and the re-generated low resolution reference image data are compared with one another to detect a defect.

(4) Analyzing the Defect (S4)

The information on the defects obtained from the high resolution optical image data and the information on the defects obtained from the low resolution optical image data are respectively sent from the comparator 117 to the defect analyzer 118 in FIG. 1.

As described above, the low resolution optical image data is acquired by using the illumination optical system 200 as a low resolution optical system. The low resolution optical system is an optical system that simulates the optical system of the exposure apparatus used when the pattern provided on the mask Ma is transferred to the wafer.

Generally, when the mask is inspected using only the high resolution optical system, to obtain an image (a wafer transfer image) representing the pattern of the mask transferred to the wafer, the wafer transfer image is estimated by simulation based on the optical image captured by the high resolution optical system. On the other hand, since the low resolution optical system simulates the optical system of the exposure apparatus as described above, the optical image captured by the low resolution optical system corresponds to the wafer transfer image. Namely, according to the low resolution optical system, the wafer transfer image is directly obtained without performing the simulation.

A defect detected by comparing the low resolution optical image data with the low resolution reference image data corresponding to the low resolution optical image data represents a defect to be detected in the wafer transfer image. Therefore, it is presumed that the detected defect will represent a defect on the wafer produced when the pattern of the mask is transferred to the wafer. On the other hand, if a defect is not detected in the low resolution optical image data, even if the defect is detected in high resolution optical image data, it is presumed that this defect will not be transferred to the wafer. Therefore, such a defect can be determined to be a fault defect which is not necessarily detected in the inspection. In this way, the transferability of a defect in the pattern of the mask Ma to the wafer can be evaluated from the information on a defect or defects detected in the high resolution optical image data and the information on the defect or defects obtained from the low resolution optical image data.

The defect analyzer 118 analyzes the defect detected in the high resolution optical image data in reference to the information on the defect or defects obtained from the low resolution optical image data. Specifically, the transferability of the defect or defects detected in the high resolution optical image data to the wafer is evaluated to determine whether the defect or defects are true or fault.

For example, if in the same pattern, a defect detected in the high resolution optical image data is not detected in the low resolution optical image data, it is presumed that this defect will not be transferred to the wafer. Therefore, the defect is determined to be a fault defect having no critical effect in practice. On the other hand, if a defect detected in the high resolution optical image data is detected also in the low resolution optical image data, it is presumed that this defect will be transferred to the wafer, and thus the defect is determined to be a true defect which is distinguished from the fault defect.

By analyzing defects in the defect analyzer 118, the true defects can be extracted from the defects detected in the optical image data obtained by the high resolution optical system. Information on the true defects is saved, for example, in the magnetic disk drive 119.

As described above, in the present embodiment, the inspection apparatus captures an optical image obtained by the high resolution optical system and an optical image obtained by the low resolution optical system. Since the high resolution optical system has high detection sensitivity, it can detect a defect in a fine pattern formed on the mask using the obtained optical image. In contrast, since the low resolution optical system simulates the optical system of the exposure apparatus used when the pattern of the mask is transferred to the wafer, the acquired optical image corresponds to the wafer transfer image. Therefore, there is no need to estimate the wafer transfer image through simulation.

In the present embodiment, when the reference image data is generated from the design data of the pattern of the mask, a correction of the design pattern data is performed in reflection of at least one of: 1) shapes and dimensions of the pattern determined in a manufacturing process of the mask, and 2) shapes and dimensions of the pattern determined in a manufacturing process of a semiconductor device which is manufactured by transferring the pattern provided on the mask to the wafer. That is, the design pattern data is corrected to reduce deviations in shapes and dimensions of the pattern produced in the manufacturing process of the mask or the manufacturing process of the semiconductor device.

As described above, the degree of roundness of corners of the pattern of the mask and the dimensions of the widths of finished lines which are produced in the manufacturing processes are added or subtracted in the pattern of the mask, and the pattern of the mask does not completely conform to the design pattern data. Furthermore, a correction of the design pattern data is sometimes made so that the pattern of the mask has predetermined shapes. Also, in such a case, the pattern of the mask will not conform to the design pattern data. According to the present embodiment, corrections are made in the design pattern data in reflection of the shapes and the dimensions of the pattern determined in the manufacturing process of the mask or in the manufacturing process of the semiconductor device. Thus, a difference between the pattern of the mask and the design pattern data can be reduced. Therefore, by comparing the reference image data generated from the corrected design pattern data with the optical image data, it becomes possible to reduce fault defects and perform an accurate inspection.

According to the results of the comparison of the high resolution optical image data and the low resolution optical image data with the reference image data, a reference image generation function is reviewed for both of the high resolution optical image data and the low resolution optical image data as needed to regenerate reference image data. With this, defects in the high resolution optical image data can be more accurately detected. Furthermore, it becomes possible to determine more accurately the influence of the transferability, i.e., whether or not the detected defect of the pattern of the mask is transferred to the wafer, by using the low resolution optical image.

In the present embodiment, the acquisition of the optical image data using the high resolution optical system may be performed independently from the acquisition of the optical image data using the low resolution optical system, or these acquisitions may be performed concurrently.

For example, first, an optical image is captured using the high resolution optical system for the illumination optical system and detection of a defect is performed for optical image data obtained from the high resolution optical image. Thereafter, optical images are captured only for portions where defects are detected in the high resolution optical image data, by using the low resolution optical system for the illumination optical system. Then, the transferability of the defects to the wafer is evaluated from the low resolution optical image data. In this case, the high resolution reference image data can be generated while acquiring the high resolution optical image data. Similarly, the low resolution reference image data can be generated while acquiring the low resolution optical image data.

For example, the inspection apparatus may be equipped with two optical systems for the high resolution optical system and the low resolution optical system to capture the low resolution optical image while capturing the high resolution optical image. According to this method, a defect that cannot be detected in the high resolution optical image data can be detected in the low resolution optical image data.

Embodiment 2

In the Embodiment 1, the transferability of a defect detected in the pattern of the mask to the wafer (a semiconductor substrate) is evaluated based on the optical image data acquired by the low resolution optical system. In the Embodiment 2, an inspection method is explained in which a shape of a defect formed when the defect is transferred to the semiconductor substrate is estimated based on a defect detected in the optical image data acquired by the high resolution optical system, and the inspection is performed by more accurately evaluating the transferability of the defect to the wafer.

An inspection method according to the present embodiment comprises acquiring optical image data (S11), generating reference image data (S12), detecting a defect (S13), estimating a wafer transfer image (S14), and analyzing the defect (S15). Hereinbelow, each of the steps will be explained.

Figure 5:
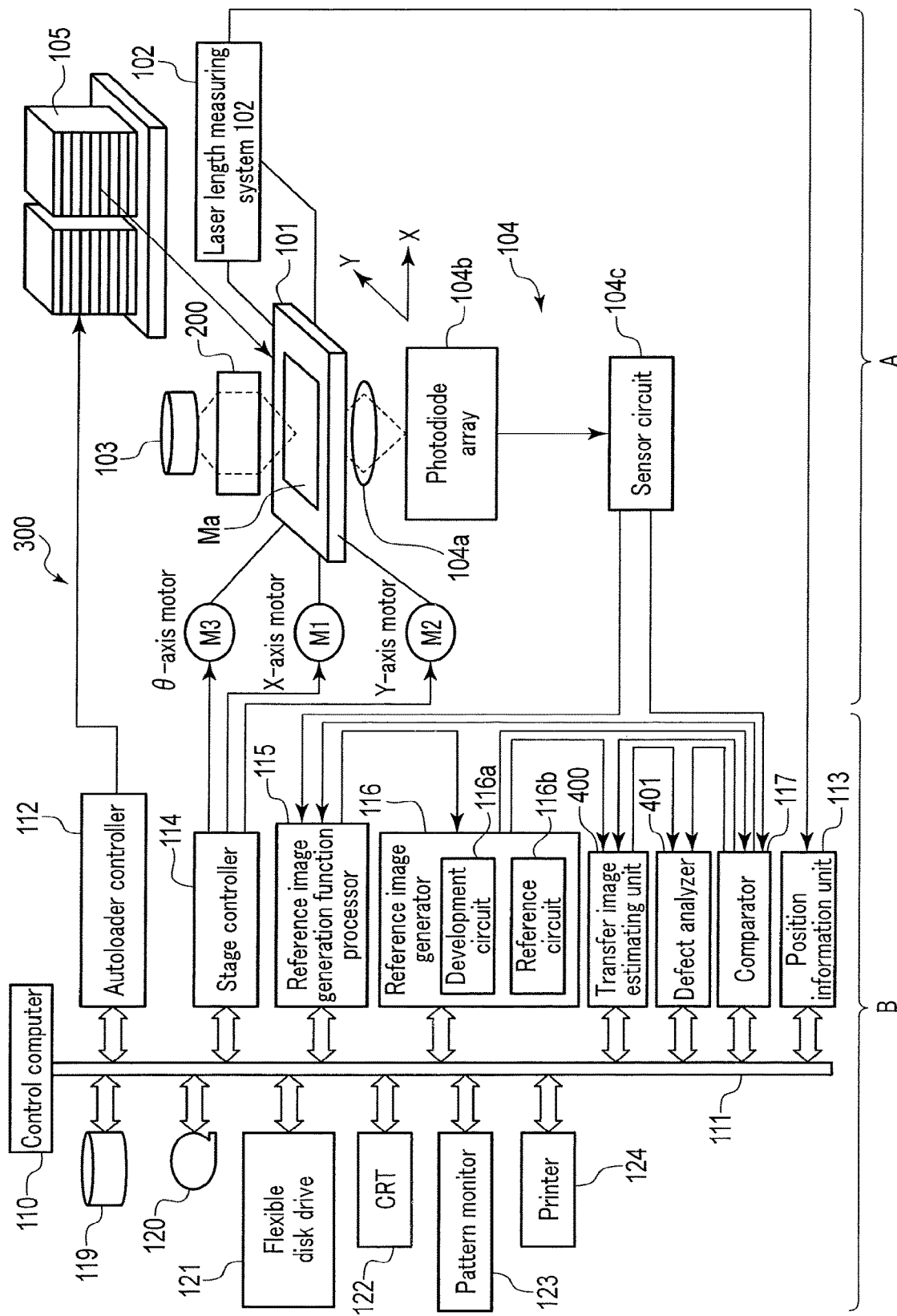
FIG. 5 is a schematic diagram of a configuration of an inspection apparatus according to a second embodiment.

FIG. 5 is a diagram showing the configuration of an inspection apparatus 300 according to the present embodiment. In this figure, portions using the same denotations as in FIG. 1 explained in Embodiment 1 indicate that they are identical ones, and thus detailed explanations thereof are omitted. FIG. is a flowchart of the inspection method according to Embodiment 2. The portions corresponding to each of the steps of S11 to S15 are indicated by being enclosed with dotted lines in the figure.

(1) Acquiring Optical Image Data (S11)

This step is similar to the acquiring optical image data (S1) explained in Embodiment 1.

Namely, in FIG. 5, light emitted by a light source 103 and transmitted through an illumination optical system 200 illuminates a mask Ma. The illumination system 200 may have a configuration similar to that explained referring to FIG. 2 in the Embodiment 1. In the present embodiment, the size of an aperture diaphragm 200d is adjusted to correspond to the high resolution optical system of Embodiment 1, specifically, so that the numerical aperture NA ranges, for example, from 0.75 to 0.85. After light transmitted through the mask Ma forms an optical image of the pattern of the mask Ma, optical image data for the optical image is output through A/D (analog/digital) conversion.

(2) Generating Reference Image Data (S12)

This step is similar to the generating reference image data (S2) explained in Embodiment 1.

Like Embodiment 1, in the present embodiment, corrections are made in the design pattern data in reflection to shapes and dimensions of the pattern determined in the manufacturing process of the mask Ma or in the manufacturing process of the semiconductor device manufactured by transferring the pattern provided on the mask to the wafer. Then, reference image data is generated using the corrected design pattern data.

The corrected design pattern data is converted into binary or multi-level image data in a development circuit 116a of a reference image generator 116. This image data is sent from the development circuit 116a to a reference circuit 116b. The reference circuit 116b performs filtering of the image data.

The determination of a reference image generation function in the filtering process is performed in the reference image generation function processor 115 in FIG. 5 in a manner similar to Embodiment 1. In the determination of the reference image generation function, for example, the illumination optical system 200 is simulated, or image-forming parameters in a photodiode array 104b are adjusted. On this occasion, it is preferred to adjust the simulation and the image-forming parameters so as to minimize a difference between the high resolution optical image data and the reference image data corresponding to the high resolution optical image data. Similarly, it is preferred to adjust the simulation and the image-forming parameters so as to minimize a difference between the low resolution optical image data and the reference image data corresponding to the low resolution optical image data. Furthermore, in addition to these adjustments, it is also preferred to adjust the position of a light receiving surface of a photodiode array 104b. On this occasion, it is more preferred to take a focus offset amount into account.

The determined reference image generation function is sent from the reference image generation function processor 115 to the reference image generator 116. Then, in the reference circuit 116b in the reference image generator 116, the image data output from the development circuit 116a is filtered using the reference image generation function. With this, the reference image data which resembles the optical image data is generated.

(3) Detecting a Defect (S13)

In this step, the optical image data obtained in acquiring the optical image data (S11) is compared with the reference image data generated in generating reference image data (S12) to detect a defect(s) in the optical image data.

Detecting a defect is performed at a comparator 117 shown in FIG. 5. Therefore, the optical image data is sent from the imaging device 104, and the reference image data is sent from the reference image generator 116, to the comparator 117. Position data obtained by measuring coordinates of the position of a stage 101 is sent from a position information unit 113 to the comparator 117.

Specific methods of the comparison and the detection of a defect are similar to the methods described in detecting a defect (S3) in Embodiment 1. In a case where for example, a number of fault defects are detected by the comparison, an instruction for re-determining the function is output from the comparator 117 to the reference image generation function processor 115 in FIG. 5. Next, in the reference image generation function processor 115, a reference image generating function is re-determined. Thereafter, in the reference image generation function processor 115, the reference image generation function is re-determined. Then, the re-determined reference image generation function is sent to the reference image generator 116, and reference image data is regenerated in the reference image generator 116. Then, in the comparator 117, the optical image data is compared with the regenerated reference image data. If a difference between the optical image data and the reference image data exceeds a predetermined threshold, the relevant portion is detected as a defect.

(4) Estimating a Wafer Transfer Image (S14)

The optical data of the defect detected at the comparator 117 and an area neighboring the defect is sent to a transfer image estimating unit 400. The corrected design pattern data is also sent to the transfer image estimating unit 400. For example, if the corrected design pattern data is stored in a magnetic disk drive 119, a control computer 110 reads the corrected design pattern data out and sends it to the transfer image estimating unit 400.

The transfer image estimating unit 400 estimates a shape of a defect, such as a defect of a convex shape and a defect of a concave shape, using the optical image data near the defect detected by the comparator 117, the reference data corresponding to the optical image data, and the corrected design pattern data. Next, the estimated shape of the defect is composed to the corrected design pattern data. Thereafter, a first wafer transfer image of the pattern to be formed when the pattern is transferred to the wafer is estimated from the composed data, using conditions in which the pattern provided on the mask Ma is transferred to the wafer.

Furthermore, the transfer image estimating unit 400 estimates, based on the corrected design pattern data, a second wafer transfer image of the pattern to be formed when the pattern is transferred to the wafer, using the conditions in which the pattern provided on the mask Ma is transferred to the wafer. The second wafer transfer image does not include information on the defect detected in the optical image data.

In the present embodiment, corrections are made to the design pattern data in reflection of shapes and dimensions of the pattern determined in the manufacturing process of the mask or in the manufacturing process of the semiconductor device manufactured by transferring the pattern provided on the mask to the wafer. Since the wafer transfer image is estimated using the corrected design pattern data, it is possible to obtain an accurate wafer transfer image by improving the accuracy of the simulation.

Examples of the conditions in which the pattern provided on the mask Ma is transferred to the wafer include photolithography conditions used when the pattern of the mask Ma is transferred to the wafer by an exposure apparatus. For a simulation of an exposed image, such as an image of a circuit pattern to be formed when the circuit pattern is transferred to the wafer by the exposure apparatus, for example, the following are incorporated herein by reference: H. H. Hopkins, "On the diffraction theory of optical images", In Proc. Royal Soc. Series A., volume 217 No. 1131, pages 408-432, 1953; N. B. Cobb, "Fast Optical and Process Proximity Correction Algorithms for Integrated Circuit Manufacturing" A dissertation submitted in partial satisfaction of the requirements for the degree of Doctor of Philosophy in Engineering: Electrical Engineering and Computer Science in the Graduate Division of the University of California at Berkeley, Spring 1988.

The optical system of the exposure apparatus is a partially coherent optical system. If a pattern drawn on a mask is transferred to the wafer by the exposure apparatus, a light intensity I (x, y) at a point (x, y) on the wafer can be obtained by calculating a value of I*(fx, fy) which represents a Fourier transformed intensity I (x, y), using the following numerical formulae, where i is a pure imaginary number.

$$I(x,y) = \iint I^*(f_x, f_y) \exp\{-2\pi i (f_x x + f_y y)\} df_x df_y$$

$$i = \sqrt{(-1)} \quad \text{(Formula 1)}$$

I*(fx, fy) is determined using the following Hopkins formulae.

$$I^*(f_x, f_y) = \iint T(f_x + f_x', f_y + f_y'; f_x, f_y) \times \quad \text{(Formula 2)}$$
$$G(f_x + f_x', f_y + f_y') \times G^*(f_x', f_y') df_x' df_y'$$

In the above Hopkins formulae, G (fx, fy) indicates a Fourier transformed mask transmission. T (f'x, f'y; fx, fy) is a Transmission Cross Coefficient, and this is calculated as follows.

$$T(f_x', f_y'; f_x'', f_y'') = \iint J_o^-(f_x, f_y) \times \quad \text{(Formula 3)}$$
$$K(f_x + f_x', f_y + f_y') \times K^*(f_x + f_x'', f_y + f_y'') df_x df_y$$

In the above formula, $J^-_0$ (fx, fy) represents a light source intensity distribution of an effective light source. K (fx, fy) represents a pupil function (i.e., a coherent transmission function). In a case where the mask transmission is optimized by changing the shape of the light source by the source mask optimization (SMO), the change in shape of the light source is reflected in the light source intensity distribution $J^-_0$ (fx, fy).

In the present embodiment, a plurality of types of defects having predetermined shapes and dimensions may be registered as program defects, and in the transfer image estimating unit 400, information on the program defects may be suitably selected and added to the corrected design pattern data. For example, a plurality of defects of a convex shape each having a different size can be incorporated into the corrected design pattern data. Then, based on the composed data, the wafer transfer image is estimated using the conditions in which the pattern provided on the mask Ma is transferred to the wafer.

(5) Analyzing the Defect (S15)

The first wafer transfer image and the second wafer transfer image obtained in the transfer image estimating unit 400 are sent to a defect analyzer 401. The defect analyzer 401 compares the first wafer transfer image with the second wafer transfer image to evaluate the transferability of the defect detected in the pattern of the mask Ma to the wafer, and determines whether or not the defect detected in the optical image data is true or fault.

The comparison between the first wafer transfer image and the send wafer transfer image is performed in a manner similar to the comparison between optical image data and reference image data in detecting a defect (S13). If a defect is detected as a result of the comparison, whether or not such a defect corresponds to the defect detected in the optical image data is examined. Then, if it is confirmed that the defect detected in the optical image data is also present in the wafer transfer image, it is presumed that the defect will be transferred to the wafer to result in a defect on the wafer. Therefore, the defect can be determined as a true defect. In contrast, if the defect detected in the optical image data is not detected as a defect in the comparison between the first transfer image and the second transfer image, it is presumed that this defect will not be transferred to the wafer. Therefore, this defect can be determined as a fault defect which is not necessarily detected in the inspection.

If a wafer transfer image is estimated by adding, to the corrected design pattern data, the program defects instead of the defects detected in the optical image data, the limit of the ability of the defect detection in the wafer transfer image is recognized. Therefore, the transferability of the defect detected in the optical image data to the wafer can be presumed in comparison with the above. For example, in a case where program defects are a plurality of defects of convex shapes each having a different size, a threshold for dimensions of the convex defects to be transferred to the wafer can be estimated from the convex defects detected in the wafer transfer image. If the dimensions of the convex defect detected in the optical image data are smaller than the threshold, it can be presumed that the defect will not be transferred to the wafer. On the other hand, if the dimensions of the convex defect detected in the optical image data are larger than the threshold, it can be presumed that the defect will be transferred to the wafer to result in a defect on the wafer.

By analyzing the defects by the defect analyzer 118, true defects can be extracted from the defects detected in the optical image data which is acquired by the optical system.

As explained above, in the present embodiment, when the reference image data is generated from the design data of the pattern of the mask, corrections are made to the design pattern data in reflection of shapes and dimensions of the pattern determined in the manufacturing process of the mask Ma or in the manufacturing process of the semiconductor device. Therefore, by comparing the reference image data generated from the corrected design pattern data with the optical image data, it becomes possible to reduce fault defects to perform an accurate inspection.

Since the wafer transfer image is estimated based on the corrected design pattern data obtained as described above, the accuracy of the simulation is improved to obtain an accurate wafer transfer image.

Furthermore, according to the present embodiment, whether or not a defect of the pattern of the mask is transferred to the wafer is evaluated relying on the wafer transfer image. Thereby, whether or not the defect detected in the optical image data is true or fault is determined. Thus, a further accurate inspection result can be obtained.

The present invention is not limited to the embodiments described above, and various modifications may be implemented without departing from the concept or scope of the present invention.

In the embodiments described above, descriptions for portions which are not directly necessary to explain the present invention, such as detailed configurations of devices and control methods, are omitted. However, it should be noted that the configurations of the devices and the control methods can be suitably selected and used if required. All inspection methods and inspection apparatuses that comprise the elements of the present invention and that can be suitably modified by a person ordinarily skilled in the art are encompassed in the scope of the present invention.

What is claimed is:

1. An inspection method comprising:
    acquiring first optical image data of a pattern arranged on a mask by irradiating the mask with light emitted by a light source via a first optical system and directing the light transmitted through or reflected by the mask to be incident on an imaging device;
    acquiring second optical image data of the pattern by irradiating the mask with light emitted by the light source via a second optical system and directing the light transmitted through or reflected by the mask to be incident on the imaging device, wherein the second optical system has a resolution lower than the first optical system and simulates an optical system of an exposure apparatus to be used to transfer the pattern of the mask to a semiconductor wafer;
    generating first reference image data corresponding to the first optical image data and second reference image data corresponding to the second optical image data based on corrected design data, wherein the corrected design data is created by correcting design data for the pattern of the mask in light of shapes and dimensions of the pattern of the mask determined according to at least one of a manufacturing process of the mask and a manufacturing process of a semiconductor device to be manufactured by transferring the pattern of the mask on the semiconductor wafer;
    detecting a defect of the pattern in the first optical image data by comparing the first optical image data with the first reference image data;
    detecting a defect of the pattern in the second optical image data by comparing the second optical image data with the second reference image data; and
    determining whether the detected defect in the first optical image data is a true defect or a false defect in reference to information of the detected defect in the second optical image data and evaluating transferability of the detected defect to the semiconductor wafer.

2. The inspection method according to claim 1, wherein the shapes and the dimensions of the pattern determined according to the manufacturing process of the semiconductor device are estimated based on a difference between a measured value and a design value of dimensions of a certain portion of the pattern of the mask.

3. The inspection method according to claim 1, wherein generating the first reference image data and the second reference image data includes filtering an image data created based on the corrected design data, and
    further comprising adjusting simulation of characteristics of the resolutions of the first optical system and the second optical system, and parameters of image generation of the imaging device so as to minimize each of a difference between the first optical image data and the first reference image data and a difference between the second optical image data the second reference image data.

4. The inspection method according to claim 2, wherein generating the first reference image data and the second reference image data includes filtering an image data created based on the corrected design data, and
    further comprising adjusting simulation of characteristics of the resolutions of the first optical system and the second optical system, and parameters of image generation of the imaging device so as to minimize each of a difference between the first optical image data and the first reference image data and a difference between the second optical image data the second reference image data.

5. An inspection method comprising:
    acquiring optical image data of a pattern arranged on a mask by irradiating the mask with light emitted by a light source via an optical system and directing the light transmitted through or reflected by the mask to be incident on an imaging device;
    generating reference image data corresponding to the optical image data based on corrected design data, wherein the corrected design data is created by correcting design data for the pattern of the mask in light of shapes and dimensions of the pattern of the mask determined according to at least one of a manufacturing process of the mask and a manufacturing process of a semiconductor device to be manufactured by transferring the pattern of the mask to a semiconductor wafer;
    detecting a defect of the pattern in the optical image data by comparing the optical image data with the reference image data;
    estimating a shape of the defect to be transferred to the semiconductor wafer by use of an optical image data of the defect of the pattern detected in the optical image data, the reference data corresponding to the optical image data, and the corrected design data of the pattern, and estimating a first transfer image as transferred to the semiconductor wafer, based on data in which information on the estimated shape of the defect is added to the corrected design data, using a condition where the pattern arranged on the mask is transferred to the semiconductor wafer;
    estimating a second transfer image of the pattern to be transferred on the semiconductor wafer, based on the corrected design data, by use of the condition where the pattern of the mask is transferred to the semiconductor wafer; and
    determining whether the detected defect is true or false by comparing the first transfer image and the second transfer image and evaluating transferability of the detected defect to the semiconductor wafer.

6. An inspection apparatus comprising:
    a light source;
    a stage on which a mask is places;
    an optical system having a variable numerical aperture and directing light emitted by the light source to irradiate the stage;
    an imaging device that acquires optical image data of the mask placed on the stage by directing light emitted by the light source, through the optical system, and transmitted through or reflected by the mask to be incident on the imaging device;
    a reference image generator that generates reference image data corresponding to the optical image data based on corrected design data, wherein the corrected design data is created by correcting design data for the pattern of the mask in light of shapes and dimensions of the pattern of the mask determined according to at least one of a manufacturing process of the mask and a manufacturing process of a semiconductor device to be manufactured by transferring the pattern of the mask to a semiconductor wafer;

a comparator that compares the optical image data with the reference image data to detect a defect of the pattern in the optical image data; and a defect analyzer that analyzes the defect detected in the comparator by comparing first optical image data acquired by the imaging device using the numerical aperture as a value that is required to detect a defect of the pattern with first reference image data generated by the reference image generator, based on information on a defect detected in the comparator by comparing a second optical image data acquired by the imaging device using the numerical aperture as a value that simulates an optical system of an exposure apparatus to be used to transfer the pattern to the semiconductor wafer with second reference image data generated by the reference image generator.

* * * * *